United States Patent [19]

Tan et al.

[11] Patent Number: 5,536,866

[45] Date of Patent: Jul. 16, 1996

[54] TRIARYLAMINE-BASED DINITRILE AND DICARBOXYLIC ACID MONOMERS

[75] Inventors: Loon-Seng Tan, Centerville; Kasturi R. Srinivasan, Fairborn, both of Ohio

[73] Assignee: The United States of America as represented by the Secretary of the Air Force, Washington, D.C.

[21] Appl. No.: 380,175

[22] Filed: Jan. 26, 1995

[51] Int. Cl.⁶ ........................ C07C 255/51; C07C 229/60
[52] U.S. Cl. .......................... 558/420; 562/454; 562/457
[58] Field of Search ............................ 558/420; 562/454, 562/457

[56] References Cited

PUBLICATIONS

T. D. Dang, S. J. Bai, D. P. Heberer, F. E. Arnold and R. J. Spry, "Ionic Conductivity of Conjugated Water–Soluble Rigid–Rod Polymers", *Journal of Polymer Science: Part B: Polymer Physics*, vol. 32, pp. 1941–1950 (1993).

Patricia A. DePra, John G. Gaudiello and Tobin J. Marks, "Conductive Polmers Based upon Rigid–Rod Ultrahigh--Modulus Macromolecules. Electrochemical Doping of Poly(p–phenylenebenzobisthiazole–2,6–diyl)(PBT)", *Macromolecules* 1988, pp. 2295–2297.

M. Ishikawa, M. Kawai and Y. Ohsawa, "Synthesis and properties of electrically conducting polytriphenylamines", *Synthetic Metals*, 40 (1991), pp. 231–238.

C. Y–C Lee, J. Swiatkiewicz, P. N. Prasad, R. Mehta and S. J. Bai, "Third order non-linear optical properties of poly–P--phenylene benzobisthiazole and its novel composite with Zytel processed via methane sulfonic acid solution extrusion", *Polymer*, 1991, vol. 32, No. 7, pp. 1195–1199.

Y. Oishi, H. Takado, M. Yoneyama, M–A Kakimoto and Y. Imai, "Preparation and Properties of New Aromatic Polyamides from 4–4'–Diaminotriphenylamine and Aromatic Dicarboxylic Acids", *Journal of Polymer Science: Part A: Polymer Chemistry*, vol. 28, pp. 1763–1769 (1990).

K. R. Srinivasan, L–S Tan, S. J. Bai and R. J. Spry, "Aromatic Benzobisthiazole Polymers and Copolymers Incorporated with Electron–rich Triarylamino Moieties", *Polymer Preprints*, vol. 35(1), pp. 501–502, 1994.

A. Troup, J. Mort, S. Grammatica and D. J. Sandman, "Direct Observation of Superexchange in a Disordered Molecular Solid", *Solid State Communications*, vol. 33, pp. 91–93 (1980).

C. S. Wang, J. Burkett, C. Y–C Lee and F. E. Arnold, "Structure and Electrical Conductivity of Ion–Implanted Rigid–Rod and Ladder Polymers", *Journal of Polymer Science: Part B: Polymer Physics*, vol. 31, pp. 1799–1807 (1993).

*Primary Examiner*—Joseph Paul Brust
*Attorney, Agent, or Firm*—Charles E. Bricker; Thomas L. Kundert

[57] ABSTRACT

Triarylamino-based dinitrile and dicarboxylic acid monomers as represented by the formula:

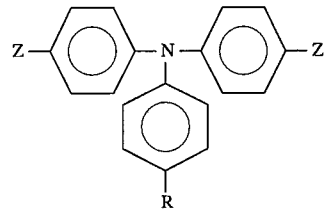

wherein Z is —CN or —COOH and R is selected from the group consisting of —H, —CH₃, —N(CH₃)₂ and —OH.

10 Claims, No Drawings

TRIARYLAMINE-BASED DINITRILE AND DICARBOXYLIC ACID MONOMERS

RIGHTS OF THE GOVERNMENT

The invention described herein may be manufactured and used by or for the Government of the United States for all governmental purposes without the payment of any royalty.

BACKGROUND OF THE INVENTION

The present invention relates to new triarylamine-based dinitrile and dicarboxylic acid monomers.

Rigid-rod poly(benzobisazole) (PBZ) polymers are well-known for their superior mechanical properties and high-temperature capability which are better than the state-of-the-art Aramids (e.g., Kevlar). The PBZ group includes poly(benzobisoxazole) (PBO), poly(benzobisthiazole) (PBT) and poly(benzobisimidazole) (PBI) polymers. These polymers have been heralded as the next-generation structural materials.

It is known that isotropic and biaxially oriented PBZ films can be rendered electrically conductive via $^{84}Kr^+$-ion implantation. Conductivity as high as 100 S/cm for biaxial oriented film has been achieved. It is also known that a PBZ film can be reduced electrochemically to a conductivity of about 20±10 S/cm. This is in accord with the fact that PBZ is known to be a π-deficient aromatic system as evidenced by both chemical and spectroscopic studies. Certain derivatized PBZ polymers have also exhibited $\chi^{(3)}$ non-linear optical (NLO) properties and ionic conductivity.

We have found that the conductivity of PBZ polymers and copolymers can be enhanced by incorporating triarylamine moieties therein.

It is therefore an object of the present invention to provide novel triarylamine-based dinitrile and dicarboxylic acid monomers.

Other objects and advantages of the present invention will be apparent to those skilled in the art.

SUMMARY OF THE INVENTION

In accordance with the present invention there are provided novel triarylamino-based dinitrile and dicarboxylic acid monomers as represented by the formula:

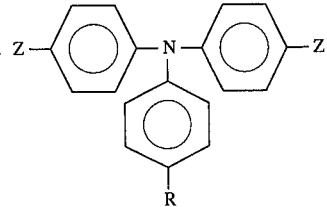

wherein Z is —CN or —COOH and R is selected from the group consisting of —H, —CH$_3$, —N(CH$_3$)$_2$ and —OH.

The triarylamine dinitrile monomers can be prepared by the cesium fluoride-promoted, aromatic nucleophilic displacement reaction of 4-fluorobenzonitrile by aniline and certain para-substituted derivatives thereof, in an aprotic polar solvent. The dicyano-triarylamine can be prepared as shown by the following reaction scheme:

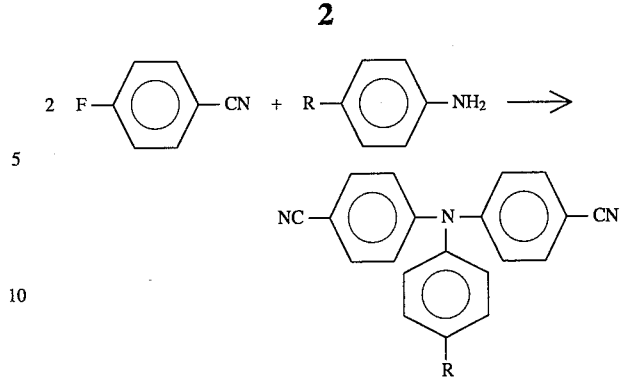

Suitable solvents for this reaction include dimethyl sulfoxide (DMSO), dimethyl acetamide (DMAc), N-methyl pyrrolidinone (NMP) and the like. In general, the reaction requires heating at reflux for about 1 to 24 hours. As shown in the Examples which follow, the monomers can be recovered from the reaction mixture using procedures known in the art. For example, the reaction mixture can be precipitated in water, then the crude product can be purified by recrystallization in appropriate solvents. Alternatively, the reaction mixture can be concentrated on a rotary evaporator, followed by vacuum-distillation of the unreacted starting materials and residual solvent. The remaining residue can then be purified by recrystallization.

The dinitriles are readily converted to the corresponding dicarboxylic acid monomers under either acidic or basic conditions. Acidic hydrolysis comprises, for example, refluxing the dicyano compound in a mixture of acetic acid and HBr. Basic hydrolysis comprises, for example, refluxing the dicyano compound in a mixture of KOH, ethylene glycol and water, followed by acidic work-up.

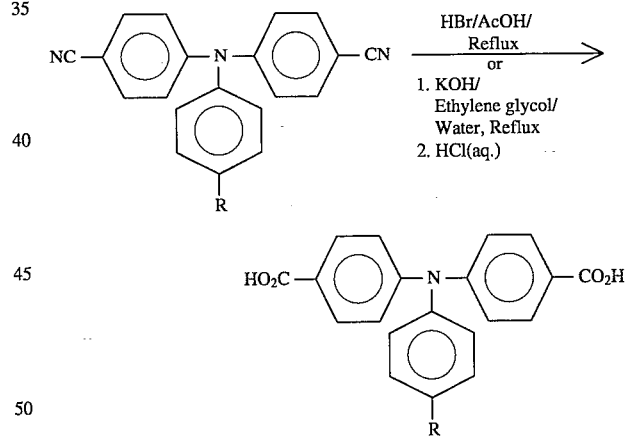

The triarylamino-based dinitrile and dicarboxylic acid monomers of this invention are useful in the preparation of benzobisoxazole and benzobisthiazole polymers and copolymers. The polymers are prepared by the polycondensation of a diaminobenzenedithiol or a diaminobenzenediol with a dicyano- or dicarboxylic acid triarylamine, as shown below. Briefly, the polymerization process comprises the following steps: (i) dehydrochlorination of a diamino-benzenedithiol dihydrochloride or a diamino-benzenediol dihydrochloride in the presence of a dinitrile or dicarboxylic acid monomer in 77% polyphosphoric acid (PPA) at 50°–65° C.; (ii) addition of P$_2$O$_5$ to raise the P$_2$O$_5$ content of the medium to 83%; (iii) chain propagation and cyclohydration; and (iv) precipitation of the polymer into water, followed by washing the polymer with ammonium hydroxide and with hot water and drying the polymer in vacuum at 110° C. The polymerization reaction is:

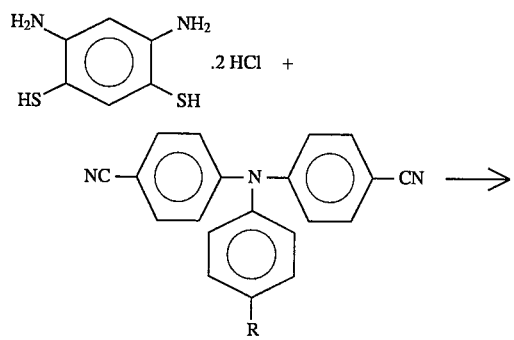

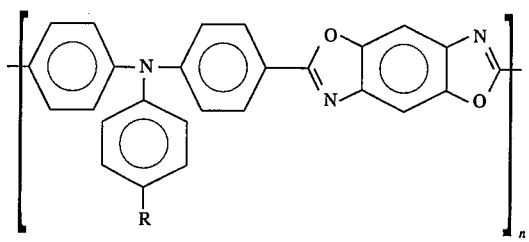

The copolymers are prepared in similar manner, for example:

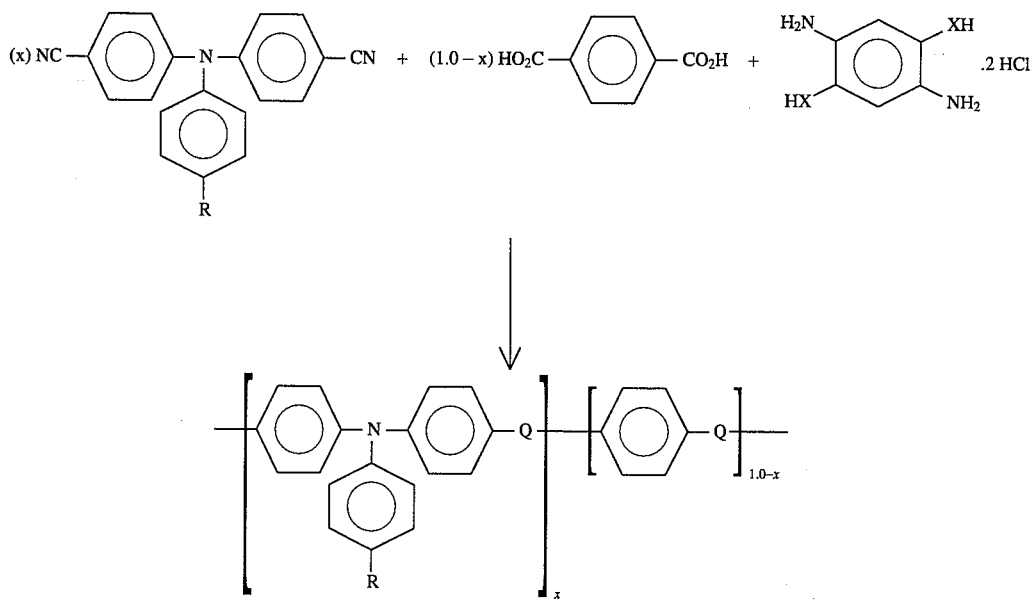

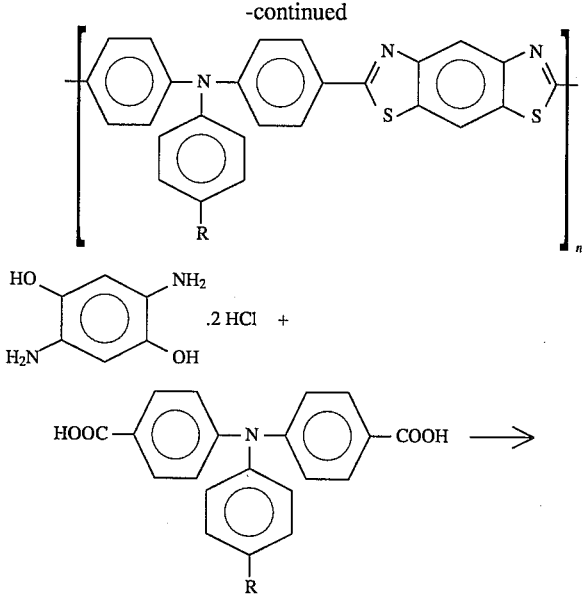

wherein x has a value of 0.01 to 0.99 and Q is

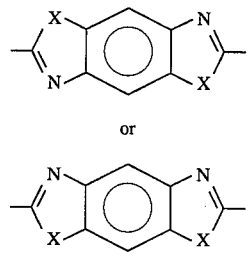

wherein X is —S— or —O—.

These polymers and copolymers can be cast into film or fiber at the time of precipitation; alternatively, they can be precipitated, washed and dried, then dissolved in a strong acid, such as methanesulfonic acid (MSA), then spin-cast into fibers or cast into film. These polymers and copolymers exhibit increased electrical conductivity, as compared to poly(p-phenylene benzobisazole) polymers. The polymers and copolymers can be treated with iodine to further increase their electrical conductivity. Preparation of the polymers and copolymers is described in application Ser.

Nos. 08/380,177 and 08/380,170, respectively, filed of even date herewith.

The following examples illustrate the invention:

EXAMPLE I

4,4'-Dicyanotriphenylamine

In a three neck round bottom flask was fitted with a mechanical stirrer, nitrogen inlet and a condenser was placed aniline (2.00 g, 21.47 mmol), 4-fluorobenzonitrile (5.70 g, 47.06 mmol), finely ground cesium fluoride (9.00 g, 59.25 mmol) and 80 mL DMSO. The reaction mixture turned yellow from colorless on heating. The mixture was held at 100° C. for 2 h, and Thin layer chromatography (TLC) of reaction mixture revealed only starting materials. The mixture was heated at 150°–155° C. for 2 h, at which stage TLC of the reaction mixture showed the appearance of a new compound. The temperature was increased to 185°–189° C. and the reaction mixture heated for 4 h. The greenish-black solution was cooled and poured over ice and stirred for 0.5 h. The resulting pale brown solid was filtered, washed several times with water and recrystallized from 2-propanol-acetone or methanol-water mixture to obtain a light yellow solid. Yield: (60%), m.p.: 191°–193° C. Elemental Analysis for $C_{20}H_{13}C_3$: Calcd.: C, 81.33%; H, 4.44%; N, 14.23%. Found: C, 81.37%; H, 4.49%; N, 14.20%. IR (KBr; cm$^{-1}$): 3060 (sp$^2$C—H), 2221 (CN). Mass spectrum: m/e: 295 (M$^+$, 100%).

EXAMPLE II

4,4'- Dicyano-4"-methyl-triphenylamine

In a 250 mL three neck round bottom flask was placed 4-methylaniline (4.00 g, 37.32 mmol), 4-fluorobenzonitrile (9.04 g, 74.64 mmol), cesium fluoride (11.50g, 75.70 mmol) and 100 mL DMAc. The light brown solution was stirred and heated slowly. On refluxing the solution for 1 h, TLC of the sample showed disappearance of the 4-methyaniline. The brown solution was refluxed for an additional 4 h, cooled and precipitated in water. The brown organic layer was extracted with ethyl acetate, washed with water, dried and roto-evaporated to obtain a yellow oil. On addition of a few drops of 1M hydrochloric acid (HCl), the yellow oil solidified. The solid was washed with water, dried and recrystallized from methanol-acetone-water to obtain a off-white crystalline solid. Yield: 4.00 g (35%), m.p.: 215°–216° C. Elemental Analysis for $C_{21}H_{15}N_3$: Calcd.: C, 81.53%; H, 4.89%; N, 13.58%. Found: C, 81.30%; H, 4.80%; N, 13.38%. IR (KBr; cm$^{-1}$): 3070 (sp$^2$C—H), 2982 (sp$^3$C—H), 2230 (CN), 1600, 1500 (C=C). Mass Spectrum: m/e: 309 (M$^+$, 100%)

EXAMPLE III

4,4'-Dicyano-4"-N,N-dimethylamino-triphenylamine

In a 250 mL three neck round bottom flask fitted with a mechanical stirrer, nitrogen inlet and a condenser was placed N,N-dimethyl-1,4-phenylenediamine (4.00 g, 29.37 mmol), 4-fluorobenzonitrile (7.20 g, 59.47 mmol), finely ground cesium fluoride (9.05 g, 59.57 mmol) and 80 mL DMSO. The green solution was stirred at 100° C. for 3 h, and TLC of the reaction mixture revealed only starting materials. The mixture was heated at 150° C. for 3 h, and then heated at reflux for 16 h. The greenish-black solution was cooled and precipitated in ice, and stirred for 0.5 h. The crude green solid was recrystallized from 2-propanol-acetone or methanol-water mixture to obtain green-yellow needles. Yield: 4.98 g (50%), m.p.: 173°–175° C. Elemental Analysis for $C_{22}H_{18}N_4$: Calcd.: C, 78.08%; H,5.36%; N, 16.56%. Found: C, 78.00%; H, 5.29%; N, 16.52%. IR (KBr, cm$^{-1}$): 3060 (sp$^2$C—H), 2850, 2790 (sp$^3$C—H), 2221 (CN). Mass Spectrum: m/e: 338 (M$^+$, 100%).

EXAMPLE IV

4,4'-Dicyano-4"-methoxy-triphenylamine

In a 250 mL three-necked, round-bottomed flask fitted with a nitrogen inlet, condenser and a magnetic stir-bar were placed 4-methoxyaniline (6.00 g, 48.70 mmol.), 4-fluorobenzonitrile (11.80 g, 97.43 mmol.), cesium fluoride (14.80 g, 97.43 mmol.) and 80 mL of NMP. The resultant mixture was heated at reflux for 16 h., cooled and then poured over ice. No precipitation occurred. Therefore, the solution was extracted with terahydrofuran-toluene mixture. The extract was then dried over MgSO$_4$ and roto-evaporated to afford a brown oil. Upon removal of residual 4-fluorobenzonitrile and NMP, an off-white solid was obtained. It was washed with methanol and dried, and then recrystallized from acetone-methanol mixture. Yield: 7.00 g (44%), m.p. 173°–176° C. Elemental Analysis for $C_{21}H_{15}N_3O$: Calcd.: C, 77.52%; H, 4.65%; N, 12.91%. Found: C, 77.42%; H, 4.61%; N, 12.86%. IR (KBr, cm$^{-1}$): 3060 (sp$^2$C—H), 2956, 2864 (sp$^3$C—H), 2237 (CN). Mass Spectrum: m/e: 363 (M$^+$, 100%).

EXAMPLE V

4,4'-Dicarboxytriphenylamine

In a 100 mL round-bottomed flask equipped with a reflux condenser and a drying tube was placed 4,4'-dicyano-triphenylamine (1.00 g, 3.38 mmol.), followed by the addition of 15 mL of glacial acetic acid and 15 mL of 48% HBr. The light green slurry was then heated to reflux, at which point all the solid dissolved, resulting in a dark green solution. Reflux was continued for an additional hour. Thin layer chromatography of the reaction mixture indicated the absence of the starting dinitrile. The dark green solution was cooled to room temperature, poured into an ice-water mixture, and neutralized with 20% aqueous ammonium hydroxide. The crude product was collected on a fritted filter funnel, washed with copious amount of water, and suction-dried overnight. Recrystallization from aqueous methanol afforded the dicarboxylic acid as a light gray, crystalline solid. Yield: 1.00 g (89%), m.p. 174°–178° C. Elemental Analysis for $C_{20}H_{15}NO_4$: Calcd.: C, 72.06%; H, 4.53%; N, 4.20%. Found: C, 71.70%; H, 4.46%; N, 4.02%. Mass Spectrum: m/e: 334 (M$^+$, 100%).

EXAMPLE VI

4,4'-Dicarboxy-4"-N,N-dimethylamino-triphenylamine (via acidic hydrolysis)

In a 250 mL round-bottomed flask, equipped with a reflux condenser and a drying tube, was placed 4,4'-dicyano-4"-N,N-dimethylaminotriphenylamine (10.00 g, 29.55 mmol.), glacial acetic acid (40 mL) and aqueous hydrobromic acid (48%, 40 mL). The resulting light green-yellow slurry was stirred magnetically. Upon heating, it became green-brown. At reflux, the reaction mixture was completely homogeneous and very dark green. After an hour of reflux, thin layer chromatography of the reaction mixture, using 1:3 (v/v) ethyl acetate/hexane as an eluent, showed the absence of the starting dicyano compound. The reaction mixture was refluxed for another 3 hours, allowed to cool to room temperature, and poured into cold water. The gray precipitate was collected on a fritted filter funnel. Upon washing with 50% ammonium hydroxide, it became yellow. The crude product was then washed with copious amount of water and suction-dried overnight. Recrystallization of the crude product from aqueous methanol provided the dicarboxylic acid as a yellow, crystalline solid. Yield: 10.45 g (94%), m.p. 226°–227° C. Elemental Analysis for $C_{22}N_{20}N_2O_4$:Calcd.: C, 70.20%; H, 5.36%; N, 7.44%. Found: C, 70.02%; H, 5.28%; N, 7.33%. Mass Spectrum: m/e: 376 ($M^+$, 100%).

EXAMPLE VII 4,4'-Dicarboxy-4"-N,N-dimethylamino-triphenylamine (via basic hydrolysis)

In a 100 mL round-bottomed flask were placed 4,4'-dicyano-4"-N',N'-dimethylamino-triphenylamine (5.00 g, 14.77 mmol.) and potassium hydroxide (3.32 g, 59.09 mmol.) and 40 mL of ethylene glycol. The resultant slurry was heated at reflux for 6 h. During reflux, the reaction mixture became completely clear and greenish yellow and water was added to the reaction mixture at a regular interval. The greenish yellow solution was cooled, poured over ice, and neutralized with 3N hydrochloric acid. The crude product was isolated by filtration, dried and recrystallized from aqueous methanol and then from ethanol/acetonitrile to provide the desired diacid as a dark green crystalline solid. Yield: 5.11 g (92%), m.p. 262°–264° C. Elemental Analysis for $C_{22}H_{20}N_2O_4$: Calcd.: C, 70.20%; H, 5.35%; N, 7.44%. Found: C, 70.08%; H, 5.29%; N, 7.30%. IR (KBr, $cm^{-1}$): 3500–2500 (OH), 1681 (C=O). Mass Spectrum: m/e:376 ($M^+$, 100%)

EXAMPLE VIII 4,4'-Dicarboxy-4"-methyl-triphenylamine

In a 100 mL round-bottomed flask were placed 4,4'-dicyano-4"-methyltriphenylamine (5.00 g, 16.16 mmol.) and potassium hydroxide (3.62 g., 64.64 mmol.) and 40 mL of ethylene glycol. The resultant slurry was heated at reflux for 16 h. During reflux, the reaction mixture became completely clear and yellow. The final yellow solution was cooled, poured over ice, and neutralized with 3N hydrochloric acid. The off-white, flaky solid was isolated by filtration, dried and recrystallized from aqueous methanol to provide the desired diacid as off-white platelets. Yield: 4.60 g (80%), m.p. 188°–190° C. Elemental Analysis for $C_{21}H_{17}NO_4$: Calcd.: C, 72.61%; H, 4.93%; N, 4.03%. Found: C, 72.48%; H, 4.87%; N, 4.00%. IR ($cm^{-1}$, KBr): 3500–2500 (OH), 1690 (C=O). Mass Spectrum: m/e:347 ($M^+$, 100%).

Various modifications may be made in the instant invention without departing from the spirit and scope of the appended claims.

We claim:

1. A triarylamino-based compound of the formula:

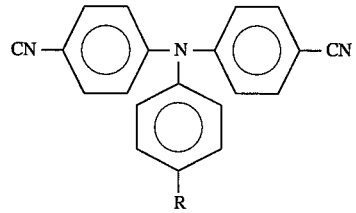

wherein R is selected from the group consisting of —H, —$CH_3$, —N($CH_3$)$_2$ and —OH.

2. The compound of claim 1 wherein R is —N($CH_3$)$_2$.
3. The compound of claim 1 wherein R is —$CH_3$.
4. The compound of claim 1 wherein R is —OH.
5. The compound of claim 1 wherein R is —H.
6. A triarylamino-based compound of the formula:

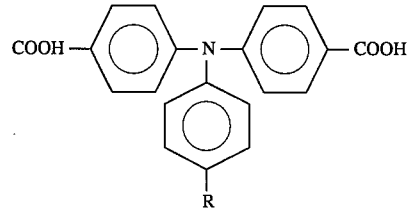

wherein R is selected from the group consisting of —H, —$CH_3$, —N($CH_3$)$_2$ and —OH.

7. The compound of claim 6 wherein R is —N($CH_3$)$_2$.
8. The compound of claim 6 wherein R is —$CH_3$.
9. The compound of claim 6 wherein R is —OH.
10. The compound of claim 6 wherein R is —H.

* * * * *